(12) United States Patent
Solomon

(10) Patent No.: US 8,733,185 B2
(45) Date of Patent: May 27, 2014

(54) MULTI-FILTER CHEMICAL SPECIATION SAMPLER AND VIRTUAL IMPACTION PARTICLE SEPARATION INLET THEREFORE

(75) Inventor: Paul Alan Solomon, Henderson, NV (US)

(73) Assignee: U.S. Environmental Protection Agency, Washington, DC (US)

( * ) Notice: Subject to any disclaimer, the term of this patent is extended or adjusted under 35 U.S.C. 154(b) by 723 days.

(21) Appl. No.: 12/575,128

(22) Filed: Oct. 7, 2009

(65) Prior Publication Data

US 2010/0089183 A1 Apr. 15, 2010

Related U.S. Application Data

(60) Provisional application No. 61/136,853, filed on Oct. 9, 2008.

(51) Int. Cl.
*G01N 1/22* (2006.01)
*G01N 1/40* (2006.01)
*G01N 1/24* (2006.01)

(52) U.S. Cl.
USPC ..................................... 73/863.22; 73/863.23

(58) Field of Classification Search
USPC ............... 73/863.12, 863.22–863.31, 863.33, 73/864.34; 55/465
See application file for complete search history.

(56) References Cited

U.S. PATENT DOCUMENTS

| 3,304,783 | A | * | 2/1967 | Quigley | 73/863.12 |
| 4,249,655 | A | * | 2/1981 | Patureau et al. | 73/863.23 X |
| 4,974,455 | A | * | 12/1990 | McGowan et al. | 73/863.23 X |
| 5,458,010 | A | * | 10/1995 | Traina et al. | 73/864.34 X |
| 6,478,856 | B1 | * | 11/2002 | Leibholz et al. | 73/863.22 X |
| 6,829,919 | B2 | | 12/2004 | Sioutas et al. | |
| 6,990,846 | B2 | | 1/2006 | Sioutas | |
| 7,325,465 | B2 | | 2/2008 | Solomon et al. | |

OTHER PUBLICATIONS

Solomon et al. "*High-Volume Dichotomous Virtual Impactor for the Fractionation and Collection of Particles According to Aerodynamic Size*", Aerosol Science and Technology, 2:455-464, in Mar. 1983.

* cited by examiner

*Primary Examiner* — Thomas P Noland

(57) ABSTRACT

A multi-filter chemical speciation sampler and a virtual impaction particle separation inlet therefore are provided. The inlet includes a housing having a bottom, a collection tube that extends through the bottom, and collection apertures formed in the bottom, arranged around the collection tube; a first plate disposed on top of the housing, having acceleration nozzles disposed at the perimeter thereof; a second plate disposed in the housing below the first plate, having a central aperture and separation apertures disposed around the central aperture. The sampler includes: an inlet; a virtual impaction separator to further fractionate the PM into a course fraction and a fine fraction; a first separation assembly to divide the course fraction into coarse aliquots, comprising first filters to collect the coarse aliquots; a second separation assembly to divide the fine fraction into fine aliquots, comprising second filters to collect the fine aliquots.

10 Claims, 4 Drawing Sheets

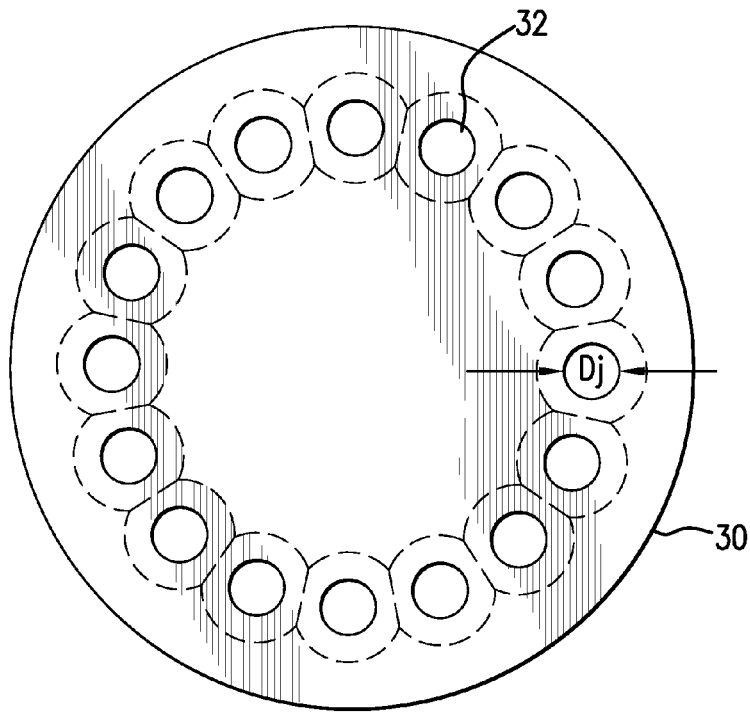 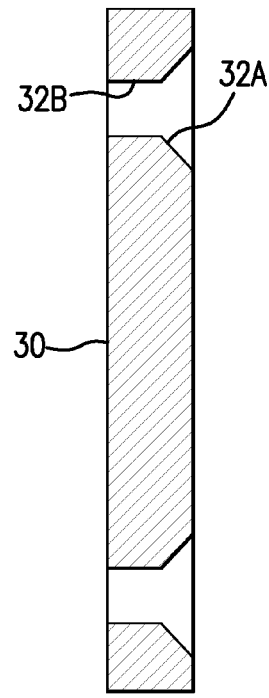
FIG.2A  FIG.2B
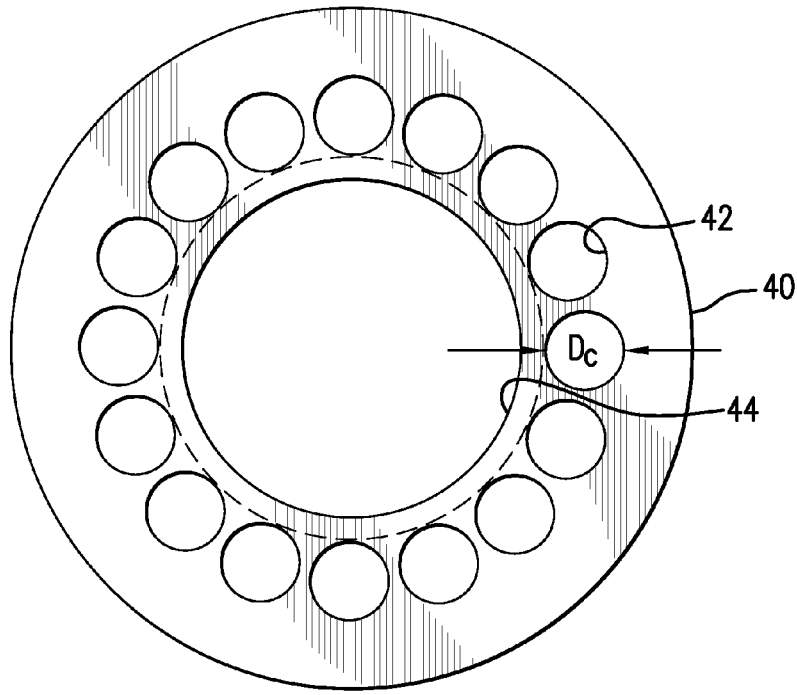 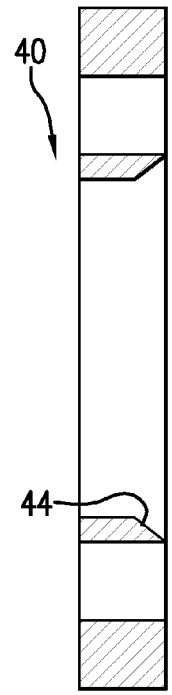
FIG.3A  FIG.3B

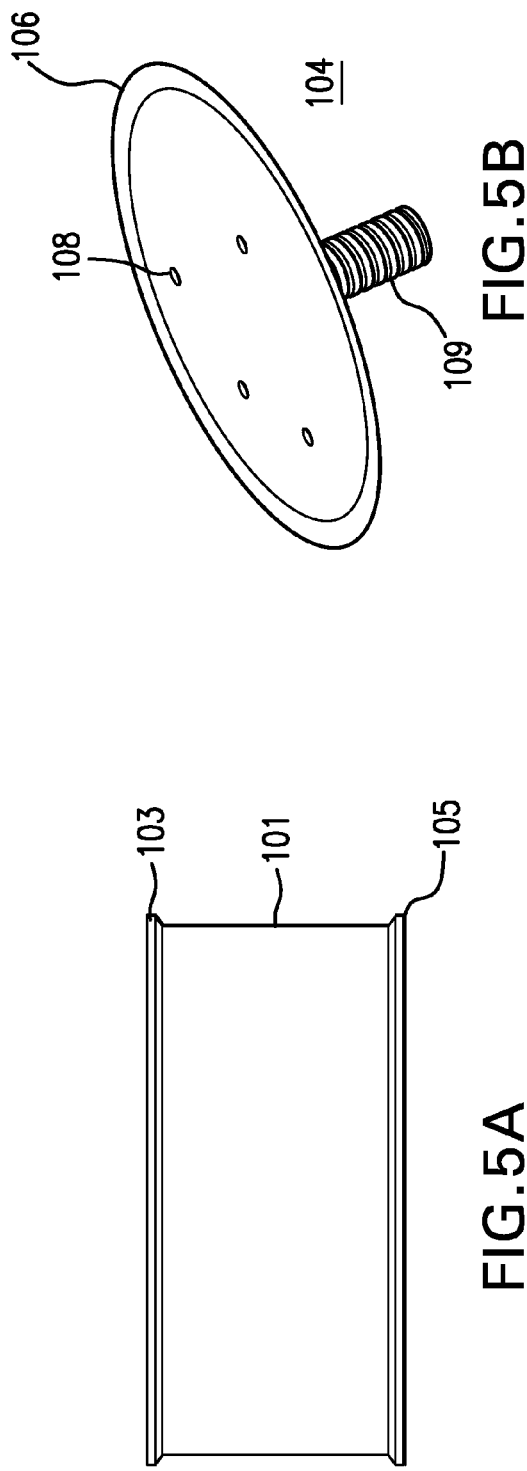

MULTI-FILTER CHEMICAL SPECIATION SAMPLER AND VIRTUAL IMPACTION PARTICLE SEPARATION INLET THEREFORE

CROSS-REFERENCE TO RELATED APPLICATION

This application claims the benefit of U.S. Provisional Application No. 61/136,853, filed Oct. 9, 2008, the disclosure of which is incorporated herein by reference.

GOVERNMENT INTEREST

This invention was made with Government support from U.S. Environmental Protection Agency (EPA), through its Office of Research and Development. The Government has certain rights in this invention.

BACKGROUND

1. Field

Aspects of the present teachings relate to multi-filter chemical speciation samplers to collect particulate matter (PM) fractions from ambient air, and virtual impaction particle separation inlets for the same.

2. Description of the Related Art

Airborne particulate matter (PM) is one of the major components of air pollution. PM includes microscopic particles in the air that are generally classified by size as being coarse PM or fine PM. The fine PM includes particles having an aerodynamic diameter (AD) of less than 2.5 microns (μm), and the coarse PM includes particles having an AD of between 2.5 and 10 μm.

PM can be released directly to the atmosphere from natural and anthropogenic sources, such as, industrial smokestacks, automobile tailpipes, wood burning, road dust, wind blown dust, and biological materials (spores and pollen), for example. PM can also form in the atmosphere from chemical reactions involving other pollutants, such as sulphur dioxide ($SO_2$), nitrogen oxides ($NO_x$), ammonia ($NH_3$), and volatile organic compounds (VOC).

Large particles (>10 μm AD) are generally filtered out by the nose. Middle-size or coarse particles (2.5 μm to 10 μm AD) are deposited in the upper airways, where they can impact on surfaces in the throat, larynx and upper branches of the lungs. Coarse PM may consist of several potentially toxic components, such as resuspended particulate matter from paved and unpaved roads, industrial materials, brake linings, tire residues, trace metals, and bio-aerosols. A considerable portion of these particles may be deposited in the upper airways and to a lesser extent into the lower airways, and may be responsible for the exacerbation of asthma and other respiratory disease. Recent data from a small number of epidemiological studies indicate that, apart from, or in addition to, the fine PM, health effects may also be closely associated with the coarse PM, to an even larger extent than to the fine PM. In vitro studies with human monocytes have shown that cellular toxicity and inflammation may also be associated with the coarse PM and its biological components.

In addition, fine PM reaches the alveoli, where it must be dealt with by macrophages from the immune system. Fine PM can be inhaled deep into the lungs and reach the critical areas where the cells replenish the blood with oxygen. They can cause breathing and respiratory symptoms, irritation, inflammation and damage to the lungs. Health studies have shown significant associations between exposure to fine PM and premature death from heart or lung disease. Fine PM also aggravates heart and lung diseases and has been linked to effects, such as cardiovascular symptoms, cardiac arrhythmias, congestive heart failure, heart attacks, respiratory symptoms, asthma attacks, and bronchitis. These effects can result in increased hospital admissions, emergency room visits, absences from school or work, and restricted activity days. Individuals that may be particularly sensitive to fine PM exposure include people with heart or lung disease, older adults, and children.

Accordingly, the U.S. Environmental Protection Agency (EPA) has published rules setting forth air quality designations and classifications for fine PM, pursuant to the National Ambient Air Quality Standards (NAAQS). The U.S. EPA has recently considered (2006) rules for coarse PM but at that time the lack of evidence associating coarse particles to health effects was lacking. The U.S. EPA will likely consider a PMc standard in the next round of NAAQS. To support this effort and learn more about PMc and health effects, the U.S. EPA is developing a coarse particle chemical speciation network, where the material collected on filters will be analyzed in the laboratory for different chemical components. Despite the growing evidence of particulate-related health effects, the paucity of information about specific biological mechanisms, associated with both fine and coarse particles, remains a critical missing link.

Accordingly, a need exists for size-fractionating PM from ambient air, separating the fractionated PM into coarse and fine fractions, and then further separating the coarse fraction into coarse aliquots collected on separate filters, which can be separately analyzed.

SUMMARY

Aspects of the present teachings relate to virtual impaction particle separation inlet comprising: a housing having a bottom, a collection tube that extends through the bottom, and collection apertures formed in the bottom, arranged around the collection tube; a first plate disposed on top of the housing, having acceleration nozzles disposed in a generally circular pattern; a second plate disposed in the housing below the first plate, having a central aperture disposed on a first end the collection tube, and separation apertures disposed around the central aperture, aligned with corresponding ones of the acceleration nozzles.

According to aspects of the present teachings, when a partial vacuum is applied to the housing, ambient air including particulate matter (PM) flows through the acceleration nozzles and is divided into a major stream and a minor stream.

According to aspects of the present teachings, the major stream flows through the central aperture and into the collection tube, and the majority of the PM in the major stream have a smaller aerodynamic diameter (AD) than that of the majority of the PM in the minor stream.

According to aspects of the present teachings, the second stream flows through the separation apertures and into the collection apertures, and at least about 90% of the fine PM in the particles in the second stream have an AD of more than about 10 μm. Ten percent of the particles less than 10 μm AD, for example, flow with the second air stream into the collection apertures. In addition, 100% of the coarse particles flow with the second air stream into the collection apertures.

Aspects of the present teachings relate to multi-filter chemical speciation sampler comprising: an inlet to fractionate PM having an AD of less than about 10 μm, for example, from other PM in ambient air, greater than about 10 μm AD, for example; a virtual impaction separator to further fractionate the fractionated PM entering the sampler, into a course fraction and a fine fraction; a first separation assembly to divide the course fraction into coarse aliquots, comprising first filters to collect each of the coarse aliquots; a second separation assembly to divide the fine fraction into fine aliquots, comprising second filters to collect each of the fine aliquots.

Additional aspects and/or advantages of the present teachings will be set forth in part in the description which follows and, in part, will be obvious from the description, or may be learned by practice of the present teachings.

BRIEF DESCRIPTION OF THE DRAWINGS

These and/or other aspects and advantages of the present teachings will become apparent and more readily appreciated from the following description of the exemplary embodiments, taken in conjunction with the accompanying drawings, of which:

FIGS. 2A and 2B respectively illustrate a top view and a side-sectional view of a first plate of the inlet of FIG. 1;

FIGS. 3A and 3B respectively illustrate a top view and a side-sectional view of a second plate of the inlet of FIG. 1;

FIGS. 5A and 5B respectively side of a body of a drum and a perspective view of a bottom plate, of the drum; and FIG. 6 illustrates a perspective view of a flow splitter.

DETAILED DESCRIPTION OF THE EXEMPLARY EMBODIMENTS

Figure 1:
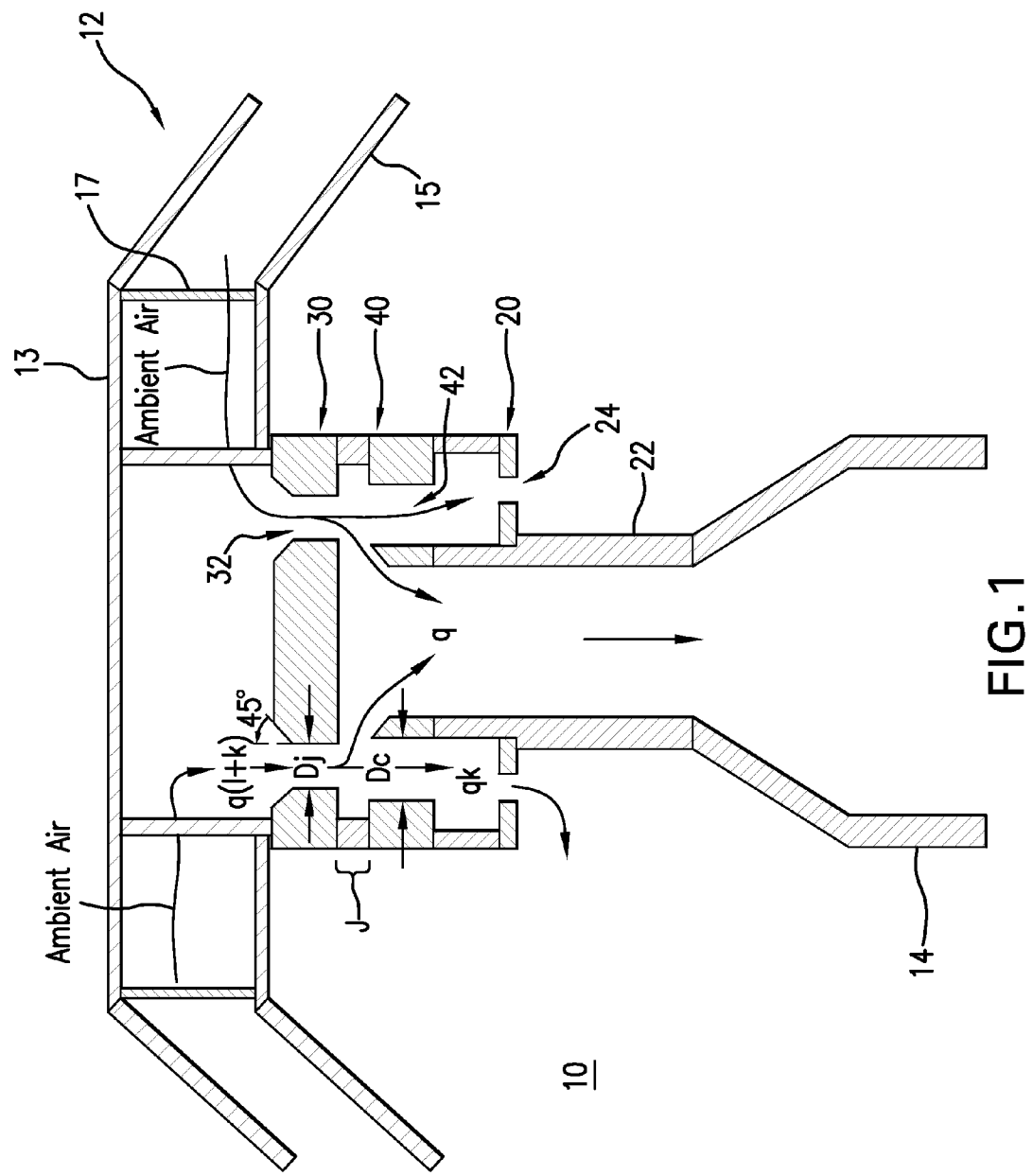
FIG. 1 illustrates a side sectional view of a virtual impaction particle separation inlet, according to aspects of the present teachings.

Reference will now be made in detail to the exemplary embodiments of the present teachings, examples of which are illustrated in the accompanying drawings, wherein like reference numerals refer to the like elements throughout. The exemplary embodiments are described below, in order to explain the aspects of the present teachings, by referring to the figures.

As used herein, "flow rate" refers to a volumetric airflow rate, but mass flow also can be applied. Particulate matter (PM) sizes are expressed in microns (µm), and refer to particulate aerodynamic diameter (AD), as conventionally used in the art. In addition, as referred to herein, "upstream" and "downstream" refer to an airflow direction through a device.

FIG. 1 illustrates a virtual impaction particle separation inlet 10, according to aspects of the present teachings. The inlet 10 may be classified by its AD cut-point. For example, the AD of particles with 50% collection efficiency would be referred to as DP50. The inlet 10 fractionates PM by virtual impaction, which eliminates particle bounce and re-entrainment problems that may be associated with real impaction particle separators. In addition, nearly all ambient PM is allowed to enter the inlet 10, with size fractionation taking place inside the inlet 10. Thus, the fractionation is independent of ambient wind speed and turbulence, obviating the need for isokinetic sampling.

The inlet 10 includes a housing 20, a first plate 30 disposed on an upstream end of the housing 20, and a second plate 40 disposed within the housing 20, downstream of the first plate 30. The housing 20 includes a collection tube 22 that extends through a central portion of the bottom of the housing 20. A plurality of collection apertures 24 are formed in the bottom of the housing 20, which are arranged around the collection tube 22. For example, from 4 to 16 collection apertures 24 may be formed in the bottom of the housing 20.

While not required in all aspects, the inlet 10 includes a precipitation guard 12, to prevent precipitants from entering the housing 20. The precipitation guard 12 includes first and second shields 13, 15, which are spaced apart, so as allow ambient air to flow therebetween and enter the inlet 10. The precipitation guard 12 also includes debris screens 17 disposed between the first and second shields 13, 15. The inlet 10 also includes an optional adapter 14 attached to the downstream end of the collection tube 22. The adaptor 14 can facilitate the connection of the inlet 10 to, for example, a standard high volume air sampler (not shown). However, it is understood that the precipitation guard 12 as shown, may be replaced by a precipitation guard different of different geometry, and the adaptor 14 may be optional and need not be included in all aspects.

FIGS. 2A and 2B respectively illustrate a top view and a side-sectional view of the first plate 30. The first plate 30 includes an upstream surface that faces away from the housing 20, a downstream surface that faces towards the housing 20, and a plurality of acceleration nozzles 32 that extend between the upstream and downstream surfaces and are evenly spaced around the center of the plate.

The acceleration nozzles 32 can each include a conical portion 32A and a cylindrical portion 32B that extends from the conical portion 32A. The acceleration nozzles 32 are disposed in an annular arrangement, such that the adjacent conical portions 32A contact one another and form an acute angle (knife edge), on the upstream surface of the first plate 30. The walls of the conical portions 32A can be disposed at, for example, an angle of approximately 40 degrees, with respect to the walls of the cylindrical portions 32B. The cylindrical portions 32B are disposed in an annular arrangement on the downstream surface of the first plate 30. There may be a smooth transition between the conical portions 32A and the cylindrical portions 32B, rather than the shown abrupt transition. In addition, while the first plate 30 is shown as being circular, the first plate 30 can have any other suitable shape, such that PM entering the inlet 10 from positions equidistant to the collection tube 22.

FIGS. 3A and 3B respectively illustrate a top view and a side-sectional view of the second plate 40. The second plate 40 includes a central aperture 44 and separation apertures 42 disposed around the central aperture, in an annular arrangement. The walls of the central aperture 44 are disposed at, for example, an angle of approximately 60 degrees, with respect to an upstream surface of the second plate 40. The edges of the separation apertures 42 are also disposed at a similar angle, so as to form sharp edges. The acceleration nozzles 32 and the separation apertures 42 are disposed in an annular arrangement, i.e., are disposed with radial symmetry around the central collection tube 22. However, the present teachings are not so limited, as the acceleration nozzles 32 and the separation apertures 42 can be disposed in any suitable arrangement, as detailed below. In addition, while the second plate 40 is shown as being circular, the second plate 40 can have any other suitable shape.

Referring again to FIG. 1, the second plate 40 is disposed in the housing 20, such that the central aperture 44 is aligned with an upstream end of the collection tube 22. The second plate 40 is disposed downstream of the first plate 30, such that each of the separation apertures 42 is aligned with (paired) a corresponding acceleration nozzle 32. In particular, the separation apertures 42 can directly or partially face the corresponding acceleration nozzles 32. In other words, the separation apertures 42 are centrally aligned with the corresponding acceleration nozzles 32. The inlet 10 can include any number of pairs of the separation apertures 42 and acceleration nozzles 32. For example, the inlet 10 can include from 2 to 36 pairs of the separation apertures 42 and acceleration nozzles 32.

When a partial vacuum is applied to the housing 20 (such as through use of a pump), the ambient air is drawn into the housing 10 through the acceleration nozzles 32. As the air is draw through the acceleration nozzles 32, the velocity thereof is increased, thereby increasing the inertia of PM included in the air, in proportion to the mass thereof. The air flow through the acceleration nozzles 32 may be laminar or turbulent.

The air is then split into major and minor streams. The major stream flows through the central aperture 44 and into the collection tube 22. The major stream generally includes from 90-98% of the total air flow into the inlet 10. The minor stream flows through the separation apertures 42 and into the collection apertures 24. Smaller PM (AD of less than about 10 µm) is primarily confined to the major air stream, and larger PM (AD of more than about 10 µm) is generally confined to the minor air stream, due to differences in the inertia thereof. In other words, the inlet 10 has a DP50 cut point of about 10 µm, as described herein. However, as discussed below, the Dp50 cut point can be adjusted, by adjusting the design parameters of the inlet 10. For example, the DP50 cut point can be from 1 µm to 10 µm, in some embodiments. In addition, all of the larger PM enters the collection apertures 24. In addition, a small amount (10% or less) of the smaller PM may also enter the collection apertures 24. However, substantially none of the larger PM enters the collection tube 22.

The collection tube 22 may be connected to an air sampler (not shown), to collect the PM in the major stream. The collection apertures 24 can also be connected to an air sampler, to collect the PM in the minor stream. Alternatively, the collection apertures 24 can be connected to one or more vacuum pumps, which can simply exhaust the minor stream. The air samplers/pumps can be used to apply the partial vacuum to the housing 20. A single pump and corresponding flow controllers can be used to create both the minor and major flow streams.

Efficient separation of the particles can occur, when a ratio of the diameter Dj of the cylindrical portions 32B to the diameter Dc of the separation apertures 42 ranges from about 1 to 1.5 and in particular, is about 1.33, for example. The lengths of the conical portions 32A and the cylindrical portions 32B (taken in a thickness direction of the first plate 30) can be approximately equal, and can also be approximately equal to the diameter Dj. The distance J, between the acceleration nozzles 32 and the separation apertures 42, can be in a range of from about 1 to 1.5 Dj, and in particular, can be 1.25 Dj, for example. The housing 20 may have a diameter of about 25 cm, for example. However, the size of the inlet 10 can be varied, according an intended application thereof.

The airflow through the acceleration nozzles 32 may be laminar or turbulent, depending on the number of nozzles (N) and the total flow rate (O). Efficient size-fractionation of particles by the inlet 10 is not affected by the occurrence of turbulent air flow through the acceleration nozzles 32.

A multi-filter chemical speciation sampler 60, according to aspects of the present teachings, is shown in FIG. 4. The sampler 60 includes: a frame 70; an inlet 11 disposed in the frame 70; a virtual impaction separator 80 connected to the inlet 11; a first separation assembly 111 attached to a first outlet of the separator 80; and a second separation assembly 113 attached to a second outlet the separator 80.

The first separation assembly 111 includes: a plenum 90 attached to the first outlet of the separator 80; a drum 100 attached to a downstream end the plenum 90; filters 120A, 120B disposed in the drum 100. While not required in all aspects, the shown first separation assembly 111 also includes a flow splitter 127 attached to downstream ends of the filters 120A, 120B; and a vacuum pump 125 attached to the flow splitter 127.

The second separation assembly 113 includes a flow splitter 110 attached to the second outlet of the separator 80 and filters 122A, 122B attached to the flow splitter 110. Although not shown, the second separation assembly 113 may also include one or more vacuum pumps and a flow controller, which are attached to the filters 122A, 122B, as shown for the first separation assembly 113.

As recited above, ambient air is drawn into the inlet 11 for PM fractionation. The PM having an AD of less than about 10 μm, for example, flows from the inlet 11 into the separator 80. According to some embodiments, the inlet 11 may be the inlet 10, or may be any suitable fractionation device having an appropriate particle size cut point. For example, the inlet 11 may be a real impaction inlet, with or without Federal Reference Method (FRM) designation.

The separator 80 can be a virtual impaction separating device as described in U.S. Pat. No. 7,325,465, the disclosure of which is incorporated herein, by reference. The separator 80 receives the PM having an AD of less than about 10 μm from the inlet 11. The separator 80 then fractionates the PM into course and fine fractions. Typically, the fine fraction includes PM having an AD of less than about 2.5 μm, and the course fraction includes PM having an AD of between about 2.5 μm and 10 μm. However, according to various aspects, the particle sizes of the course and fine fractions may be changed.

The flow split between the fine and coarse fractions can range from between 2% to 10%. In other words, between about 90% and 98% of airflow is directed to the plenum 90, with a corresponding amount of airflow (i.e., 10% to 2%) being directed to the flow splitter 110. Lower flow splits to the coarse fraction minimize the amount of fine PM collected with the coarse PM. This concentration value is corrected based on the concentration of particles observed in the fine fraction. For example, if the flow split is 10%, then 10% of the fine concentration value can be subtracted from the coarse fraction.

The course fraction exits the bottom of the separator 80 and is drawn into the plenum 90. The plenum 90 is generally a conical tube. Ends of the plenum 90 can be configured to mate with the separator 80 and the drum 100, and thereby form airtight seals. According to some aspects, tri-clamps or the like can be used to connect the plenum 90. The course fraction is drawn through the plenum 90 and into the drum 100. Due to the shape of the plenum 90, the particles of the course fraction are spread evenly in the space above the filters 120A, 120B, such that homogenous deposits of the coarse PM are collected on the filters 120A, 120B.

FIG. 5A illustrates a side view of a main body 101 of the drum 100, and FIG. 5B illustrates a perspective view of a bottom plate 104 of the drum 100. Referring to FIG. 5A, the main body 101 is generally cylindrical. Upstream and downstream edges 103, 105 of the main body 101 are beveled, so as to respectively form an airtight seal with the plenum 90 and the bottom plate 104.

Referring to FIG. 5B, the bottom plate 104 includes a plurality of apertures 108 and a positioning screw 109. The bottom plate 104 has a beveled edge 106, which corresponds to the downstream edge 105 of the main body 104.

Referring to FIGS. 4, 5A, and 5B, the filters 120A, 120B are housed in the main body 101 and face the plenum 90. In particular, the filters 120A, 120B may include, for example, a 102 mm filter 120A and three 47 mm filters 120B. However the present teachings are not limited to any particular arrangement, number, or type of filter. The filters 120A, 120B are seated in corresponding ones of the apertures 108 formed in the bottom plate 104. The apertures 108 may be designed to form an airtight seal with the corresponding filters 120A, 120B.

Downstream ends of the filters 120A, 120B are connected to the vacuum pump 125, which draws the coarse fraction though the filters 120A, 120B, to collect the coarse fraction. In some aspects, each of the filters 120A, 120B can each be connected to a separate pump. In other aspects, the flow controller 127 is disposed between the pump 125 and the filters 120A, 120B. The flow controller 127 can be, for example, a volumetric or mass flow controller. In particular, the flow controller 127 may be a flow splitter 127 to direct appropriate flows through each of the filters 120A, 120B.

While not required in all aspects, the shown sampler 60 includes a guide member 200 that is rotatably attached to the frame 70. The screw 109 is rotatably seated in the guide member 200, such that the bottom plate 104 can be moved with respect to the main body 101. The guide member 200 may be rotated, such that the bottom plate 104 can be moved out of the frame 70, to allow for easy access to the filters 120A, 120B.

Figure 4:
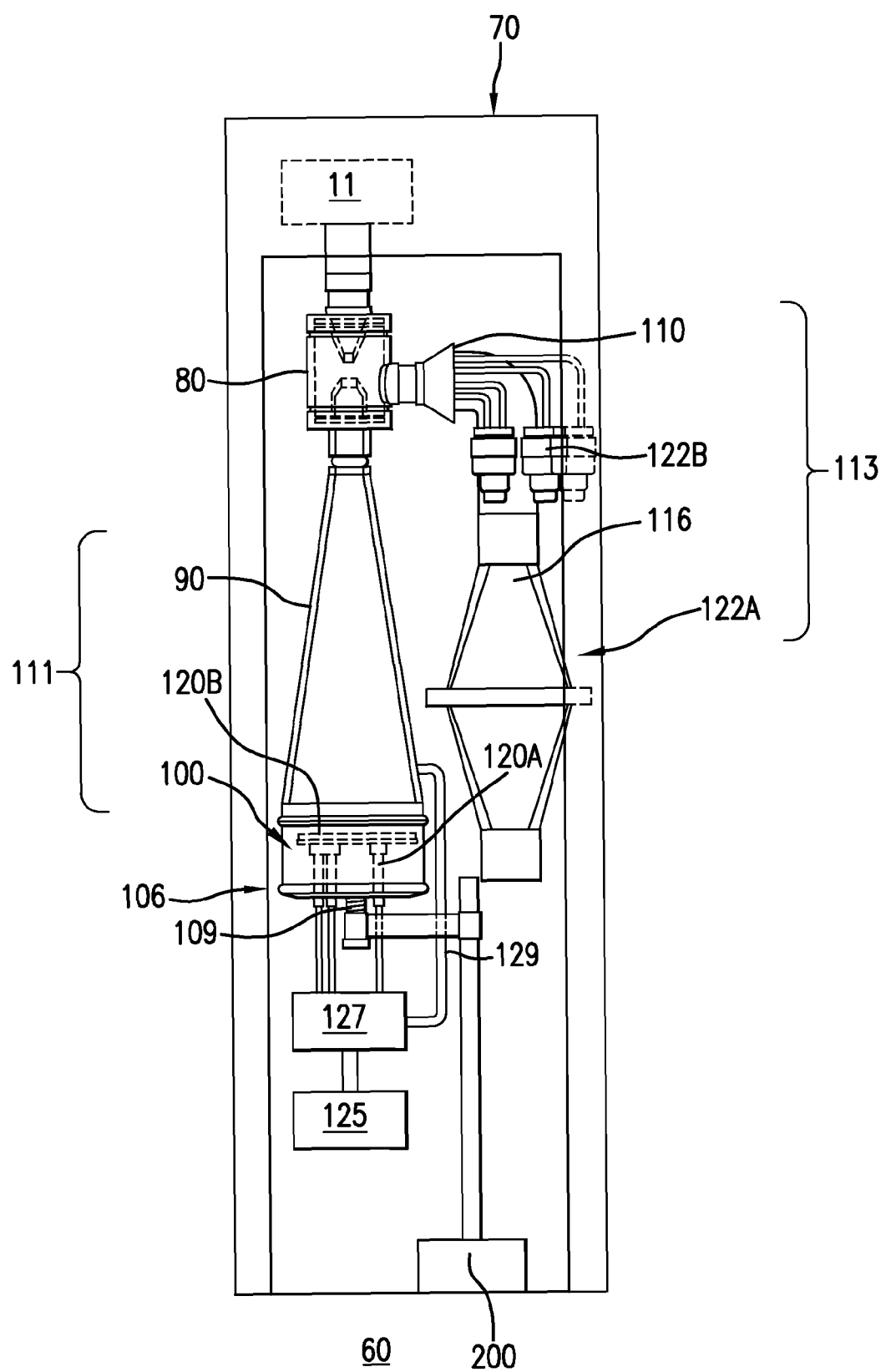
FIG. 4 illustrates a multi-filter chemical speciation sampler, according to aspects of the present teachings.

FIG. 6 illustrates a perspective view of the flow splitter 110. Referring FIGS. 4 and 6, the fine fraction exits the separator 80 and is drawn into the flow splitter 110. The flow splitter 110 includes a central aperture 112 and peripheral apertures 114. The fine fraction is divided between the apertures 112, 114 and then carried to filters. In particular, the central aperture 112 is connected to an 8×10 inch filter 122A, for example, and the peripheral apertures 114 are each connected to separate circular 47 mm diameter filters 122B, for example. The flow split between the central aperture 112 and the peripheral apertures 114 can be set according to the types of filters attached thereto, as recited above. The filters 122A, 122B are then connected to one or more vacuum pumps (not shown), and optionally a flow controller, in a manner similar to the filters 120A, 120B. The flow splitter 110 may be an ABC3000 flow splitter (URG, Durham, N.C.)

The various filters described herein can be any suitable type of filter, such as, filters made of Teflon, quartz-fiber, nylon, nucleopore, cellulose, polyurethane, or the like. In some aspects, different types of filters are simultaneously employed to collect the coarse and/or fine fractions as desired, to achieve suitable chemical analysis of the collected PM and thus, obtain a nearly complete mass balance of the collected PM. Herein, the mass balance refers to a comparison between the sum of the PM species measured, to the total mass measured of the collected PM. The sampler 60 can include a denuder on any or all of the flow paths to the various filters. The filters can be housed in filter cartridges. The filter cartridges may each include multiple filters in series as needed, to obtain chemical components of the collected PM. The sampler 60 may also include one or more bypass lines 129, to control the air flow through the filters. The bypass line 129 may extend between the plenum 90 or base plate 104, and the flow splitter 127 or the pump 125.

Because the drum 100 houses multiple filters 120A, 120B, the coarse fraction in the plenum 90 can be divided amongst a number of separate streams and drawn into the corresponding filters 120A, 120B that correspond thereto. The flow splitter 127 can be used to obtain any number of desired flow splits.

The shown sampler 60 is designed based on air flows of, for example, 400 liters per minute (Lpm) and 1000 Lpm through the inlet 10, although any flow rate is possible. At 400 Lpm, 20.1 Lpm (5%) of the air flow is diverted by the separator 80 into the plenum 90. With three of the filters 120A, 120B (a three-way split), 6.7 Lpm pass through each filter 120A, 120B. A 20.1 Lpm flow split is also acceptable at 350 Lpm (flow split is 5.8%). The flow rate of 6.7 Lpm matches the current widely used MetOne PM2.5 chemical speciation sampler. At 1000 Lpm, 50.1 LPM allows for a 3-way flow split of 16.7 Lpm. This flow rate matches the Federal Reference Methods for coarse (PM10 PM2.5) and fine (PM2.5) fractions, the former by the difference between PM10 and PM2.5. At 10% flow split for the coarse fractions at 1000 Lpm, the additional fraction can be collected by a fourth filter, at a higher flow rate (5% of the total flow, e.g., 49.9 Lpm) and used, for example, for ultra-trace organic species or trace metals analyses or used by health effects researchers for biological analysis or toxicological animal testing.

EXAMPLES

The Table 1 includes exemplary design parameters for inlets of Examples 1-3, according to aspects of the present teachings. Example 2 included an inlet having 16 acceleration nozzle/separation aperture pairs, as shown in FIG. 1, and Examples 1, and 3 included inlets respectively including 8 and 36 acceleration nozzle/separation aperture pairs. The inlets of Examples 1-3 were connected to high volume air samplers. A flow rate of 1190 l/min was 1.05 times the actual flow rate of the samplers, to account for the 5% lost to the particle flow through collection apertures thereof.

TABLE I

| Design Parameters for Virtual Impactor Inlets (10 μm AD cut point) | | | |
|---|---|---|---|
| Examples | 1 | 2 | 3 |
| Nozzle Number | 8 | 16 | 36 |
| $D_j$ (cm) | 1.861 | 1.477 | 1.127 |
| $D_c$ (cm) | 2.481 | 1.969 | 1.502 |
| $Re_j$ | 11,250 | 7085 | 4127 |

As shown in Table 1, the Dj values were calculated using Ranz and Wong classical impaction theory of (1952) and assumed a $\psi_{50}$ value of 0.15 for the impaction parameter ($\psi_{50}$ is proportional to $QD_{P50}/ND^3_j$), for the most commonly employed flow rate of a high volume sampler (1130 l/min or 40 cfm), and a $D_{P50}$ of 10 μm AD. Small adjustments can be made to $D_j$ and $D_c$ (e.g., a smaller value for $D_j$ will yield a lower cut point for the same N and Q), to obtain a desired size separation. Because $\psi_{50}$ varies for different design parameter sets, a laboratory calibration employing monodisperse and/or polydisperse aerosols may be used to determine the actual cut point and efficiency of fractionation.

The suggested existence of laminar or turbulent flow through the acceleration nozzles was determined by calculating the Reynolds number $Re_j$ ($Re_j=140.7Q/D_j$ when Q is given in l/min and $D_j$ in cm). Reynolds numbers below 2000 indicate laminar flow, whereas Reynolds numbers greater than 5000 usually indicate turbulent flow. Round nozzle turbulent flow impactors have been shown to work efficiently (Solomon et al. 1983).

Table I lists the Reynolds number values as calculated for the flow (Q/N) through the acceleration nozzle(s). As can be seen, Examples 1-3 operated under turbulent flow.

Although a few exemplary embodiments of the present teachings have been shown and described, it would be appreciated by those skilled in the art that changes may be made in these exemplary embodiments, without departing from the principles and spirit of the present teachings, the scope of which is defined in the claims and their equivalents.

What is claimed is:

1. A multi-filter chemical speciation sampler, comprising:
   an inlet to separate particulate matter (PM) having an aerodynamic diameter (AD) of less than a predetermined size from ambient air;
   a virtual impaction separator connected to the inlet, to fractionate the PM received through the inlet, into a course fraction and a fine fraction;
   a first separation assembly to divide the course fraction into coarse aliquots, comprising first filters to collect the each of the coarse aliquots; and
   a second separation assembly to divide the fine fraction into fine aliquots, comprising second filters to collect each of the fine aliquots.

2. The particle sampler of claim 1, wherein the inlet comprises:
   a real impaction inlet; or
   a virtual impaction inlet comprising:
      a housing having a bottom, a collection tube that extends through the bottom, and collection apertures formed in the bottom, arranged around the collection tube;
      a first plate disposed on top of the housing, having acceleration nozzles disposed around the perimeter of the first plate; and
      a second plate disposed in the housing below the first plate, having a central aperture disposed on an upstream end the collection tube, and separation apertures disposed around the central aperture and aligned with corresponding ones of the acceleration nozzles.

3. The particle sampler of claim 1, wherein the first separation assembly comprises:
   a plenum to collect the course fraction from the separator;
   a drum to house the first filters, to receive the course fraction from the plenum, and to divide the course stream into the course aliquots, such that the first filters can be used to determine a generally complete mass balance of the collected coarse fraction.

4. The particle sampler of claim 3, wherein the plenum is conical and disperses the coarse fraction above an upstream end of the drum, such that the coarse aliquots are homogenously collected on the first filters.

5. The particle sampler of claim 3, wherein the drum comprises:
   a main body; and
   a bottom plate disposed on a downstream end of the main body and having apertures,
   wherein the first filters are seated in the apertures of the bottom plate and face the plenum.

6. The particle sampler of claim 1, wherein:
   the majority of the PM in the course fraction has an AD of from about 2.5 µm to about 10 µm; and
   the majority of the PM in the fine fraction has an AD of less than about 2.5 µm.

7. The particle sampler of claim 1, wherein the first separation assembly comprises:
   a flow splitter to divide the fine stream into fine sub-streams, wherein the second filters collect the PM from corresponding ones of the fine sub-streams.

8. The particle sampler of claim 7, wherein the predetermined size of the AD is less than about 10 µm.

9. The particle sampler of claim 1, further comprising a bypass to control airflow to the first or second filters.

10. The particle sampler of claim 1, wherein the first filters comprise at least 2 different types of filters.

* * * * *